United States Patent [19]

Brantl et al.

[11] Patent Number: 4,826,686
[45] Date of Patent: May 2, 1989

[54] THERAPEUTIC SYSTEM

[75] Inventors: Victor Brantl, Wiesbaden; Volkmar Haselbarth, Gau-Algesheim; Bernd Zierenberg, Bingen/Rhein, all of Fed. Rep. of Germany

[73] Assignee: Boehringer Ingelheim KG, Ingelheim am Rhein, Fed. Rep. of Germany

[21] Appl. No.: 937,160

[22] Filed: Dec. 2, 1986

[30] Foreign Application Priority Data

Dec. 14, 1985 [DE] Fed. Rep. of Germany ....... 3544311

[51] Int. Cl.$^4$ .............................................. A61F 13/00
[52] U.S. Cl. .................................... 424/448; 424/486; 424/449
[58] Field of Search ................................ 424/448, 449

[56] References Cited

U.S. PATENT DOCUMENTS 4,400,378  8/1983  Innemee ............................... 514/213
4,421,737  12/1983  Ito et al. ............................... 424/449
4,685,911  8/1987  Konno et al. ........................ 424/449
4,690,683  10/1987  Chien et al. ......................... 424/448

Primary Examiner—Thurman K. Page
Assistant Examiner—L. R. Horne
Attorney, Agent, or Firm—David E. Frankhouser; Alan R. Stempel; Mary-Ellen M. Timbers

[57] ABSTRACT

This invention relates to the transdermal administration of compounds of general formula I

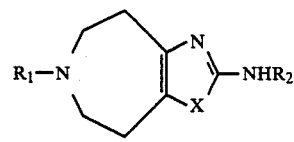

wherein $R_1$, $R_2$ and X have the meanings given in the text, and to a therapeutic system for the transdermal administration of this compound.

8 Claims, No Drawings

THERAPEUTIC SYSTEM

The invention relates to the use of compounds of general formula

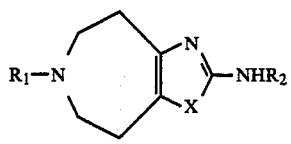

the acid addition salts thereof with physiologically acceptable inorqanic or organic acids, wherein $R_1$ represents a hydrogen atom, a straight-chained or branched alkyl group with 1 to 4 carbon atoms optionally substituted by a hydroxyl group, an allyl, cycloalkyl, hexahydrobenzyl, phenyl, phenylethyl or benzyl group, whilst the benzyl group may be substituted in the nucleus by one or two halogen atoms or by 1 to 3 methoxy groups, by a trifluoromethyl or alkyl group with 1 to 3 carbon atoms, and if X represents a sulphur atom, $R_2$ represents a hydrogen atom, a straight-chained or branched alkyl group with 1 to 5 carbon atoms, an allyl, cycloalkyl, phenyl, benzyl or phenylethyl group, or if X represents an oxygen atom, $R_2$ represents a hydrogen atom, for transdermal application in the treatment of diseases.

Preferred compounds are 2-amino-6-ethyl-4,5,7,8-tetrahydro-6H-oxazolo[5,4-d]azepine and 6-allyl-2-amino-4,5,7, 8-tetrahydro-6H-thiazolo[5,4-d]azepine and optionally the acid additon salts thereof.

The invention further relates to a therapeutic system for the release of an active substance through the skin over a fairly long period of time, particularly of compounds of general formula I, particularly 2-amino-6-ethyl-4,5,7,8-tetrahydro-6-H-oxazolo[5,4-d]azepine and also 6-allyl-2-amino-4,5,7,8-tetrahydro-6H-thiazolo[5,4-d]azepine and optionally the acid addition salts thereof.

The pharmacological properties of these named substances and the derivatives thereof are known from German Offenlegungsschrift No. 20 40 510, which describes both antitussive and hypotensive properties. A delayed-release form for the oral treatment of hypertension and angina pectoris is disclosed in DE-A No. 28 36 387.

Furthermore, 2-amino-6-ethyl-4,5,7,8-tetrahydro-6H-oxazolo[4,5-d]azepine and also 6-allyl-2-amino-4,5,7,8-tetrahydro-6H-thioazolo[5,4-d]azepine are described as B-HT 933 and B-HT 920, respectively, in numerous scientific publications.

It has not been known hitherto to administer the compounds known from DE-A No. 20 40 510, particularly 2-amino-6-ethyl-4,5,7,8-tetrahydro-6H-oxazolo[5,4-d]azepine and 6-allyl-2-amino-4,5,7,8-tetrahydro-6H-thiazolo[5,4-d]azepine transdermally, thereby avoiding the side-effects which occur in oral therapy, such as dryness of the mouth or sedation.

The success of transdermal therapy depends on various factors. For one thing, the active substance must be capable of being stored in a sufficiently high concentration in the therapeutic system in order to form a deposit of active substance, and on the other hand only controlled release and unobstructed penetration through the skin can build up a therapeutically effective blood level in the body. A further prerequisite is that the active substance must not damage the skin either on its own or in conjunction with the therapeutic system, i.e. it must not cause irritation, allergies or sensitisation.

The compounds used according to the invention, particularly 2-amino-6-ethyl-4,5,7,8-tetrahydro-6H-oxazolo[5,4-d]azepine and 6-allyl-2-amino-4,5,7,8-tetrahydro-6H-thiazolo[5,4-d]azepine, unexpectedly satisfy these conditions.

Numerous therapeutic systems in the form of skin plasters or bandages are already known which are suitable for the transdermal administration of active substances, especially nitroglycerine. Thus, for example, German Patent No. 21 35 533 describes an adhesive dressing for the administration of pharmaceutical compositions with a systemic effect, which contains, as its characteristically essential feature, a diffusion membane for controlling the release of active substance between the storage layer containing the active substance and the adhesive layer.

It is also known from European Patent No. 33 615 that the controlling function of the membrane may also be assumed by the adhesive contact surface. Therapeutic systems which contain the active substance in the form of micro-encapsulated particles are known, for example, from U.S. Pat. No. 3,742,951.

In view of the requirements imposed on drug safety, the properties of a transdermal therapeutic system should not change, with regard to the release characteristics and the stability of the active substance, even after a long period of time (e.g. caused by periods of storage).

Contrary to expectations, the therapeutic system prepared, by the process disclosed in DE-A No. 32 04 551, from a freeze-dried latex of a copolymer of methyl and/or ethyl esters of acrylic and methacrylic acid and the active substance, such as 2-amino-6-ethyl-4,5,7,8-tetrahydro-6H-oxazolo[5,4-d]azepine, does not have the required stability. After only a short time, brownish discoloration indicates decomposition of the active substance, with the result that the product is no longer acceptable for use as a pharmaceutical preparation. Similar behaviour is observed when using 6-allyl-2-amino-4,5,7,8-tetrahydro-6H-thiazolo[5,4-d]azepine.

Surprisingly, these disadvantages are avoided with the therapeutic system according to the invention.

It has now been found that the problems of stability described above can be resolved if the reservoir layer containing the active substance consists of an emulsion polymer or copolymer and a copolymer based on methacrylic acid esters with basic end groups or a small amount of a organic nitrogen-containing base.

The present invention therefore also relates to a therapeutic system in the form of a skin plaster consisting of a backing layer impervious to the active substance, a reservoir layer containing the active substance, a protective film which is to be removed and means for securing to the skin, the active substance containing reservoir layer consisting of an emulsion polymer or copolymer and a copolymer based on methacrylic acid esters with basic end groups, or, instead of the basic end groups, a small amount of an organic nitrogen-containing base.

Preferred active substances are the compounds of general formula I; 2-amino-6-ethyl-4,5,7,8-tetrahydro-6H-oxazolo[5,4-d]azepine and 6-allyl-2-amino-4,5,7,8-tetrahydro-6H-thiazolo[5,4-d]azepine are particularly preferred.

Preferred emulsion polymers of the embodiment of the therapeutic system according to the invention are PVC, polylactides, polystyrene, polyvinylacetate, polybutadiene, polyacrylonitrile, polyvinyl esters, polyvinyl ethers and the copolymers thereof.

Emulsion-polymerised copolymers of methyl and/or ethyl esters of acrylic and methacrylic acid are particularly preferred.

The preferred copolymer with basic end groups is a copolymer based on dimethylaminoethylmethylacrylate and neutral methacrylic acid esters of the general structure with sub-units A and B

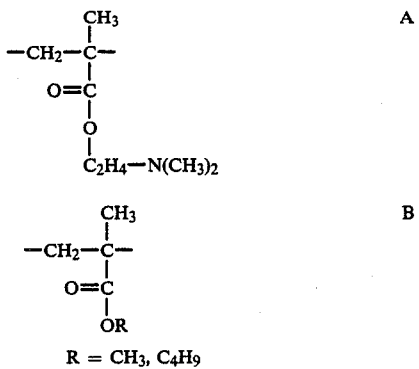

with an average molecular weight of about 150,000, as marketed, for example, by Messrs. Rohm of Darmstadt under the trade mark Eudragit ® E 100.

According to the invention the proportion of copolymer with the basic end groups is between 1 and 50% by weight, preferably from 5 to 10% by weight, based on the total polymer content of the reservoir layer.

In order to stabilize the active substance instead of a copolymer with basic end groups 0.5 to 5.0% by weight, based on the quantity of active substance, of a suitable organic base which is harmless for transdermal administration may be added to the reservoir layer.

Organic bases of general formula

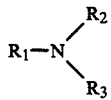

wherein $R_1$, $R_2$ and $R_3$ independently of one another represent hydrogen, a branched or unbranched alkyl or hydroxyalkyl group with 1 to 5 carbon atoms, are preferred. Isopropylamine is particularly preferred, whilst triethanolamine and tris(hydroxymethyl)-aminomethane are especially preferred.

The concentration of active substance in the reservoir layer should be in the range from 0.5 to 6 mg, preferably between 1 and 4 mg per cm², for a reservoir layer having a thickness of between 40 and 300 microns, preferably between 50 and 200 microns.

If desired, so-called solution enhancers may be added, which promote diffusion of the pharmaceutically active substance through the skin. The following compounds are particularly preferred: dimethyl lauramide, 1-dodecylazocycloheptan-2-one, glycerol dimethyl ketal, isopropyl myristate and N,N-diethyl-toluamide (J. Pharm. Sci., Vol. 71, 1211 (1982)).

The backing layer, impervious to the active substance, of the system according to the invention preferably consists of a laminate of a metal foil such as aluminium and a polymer film. Preferred polymers include high and low pressure polyethylene, polypropylene, polyvinyl chloride and polyethylene terephthalic acid.

In a preferred embodiment of the system according to the invention, the backing layer which is impervious to active substance is designed so that its surface area is greater than that of the reservoir layer and its underside is coated with a physiologically harmless adhesive. A backing layer of this kind serves simultaneously to fix the reservoir layer containing the active substance and to secure the system to the skin. Suitable adhesives include, for example, acrylic resin dispersions such as Plex ® 4853 made by Messrs. Rohm of Darmstadt.

If desired, a support layer, impervious to the active substance, consisting of a laminate of a thin aluminium foil and a polyethylene film may be provided between the active substance containing reservoir layer and the backing layer. In this case, the backing layer has a larger surface area than the reservoir layer and consists of a woven or non-woven fabric the reverse of which is coated with an adhesive. In another embodiment the system according to the invention may consist of a backing layer which is impervious to the active substance, a reservoir layer and an adhesive layer. Adhesives which permit unobstructed diffusion of the active substance are known in the art.

The release of active substance from the system according to the invention may be controlled by a suitable choice of physical parameters of the emulsion polymers used. These include varying the glass temperature by a suitable choice of monomer composition and varying the particle size of the polymer particles, which may be achieved by means of the reaction conditions during polymerisation.

An increase in the glass temperature will be accompanied by a reduction in the rate of release, a decrease in the particle size will be accompanied by an increase in the rate of release.

The possibility of freely adjusting the release of active substance from the therapeutic system described above by means of the above-mentioned parameters within a wide range means that the system can be optimally adapted to the complaint which is to be treated.

As already pointed out, the preparation of compounds of general formula I, particularly 2-amino-6-ethyl-4,5,7,8-tetrahydro-6H-oxazolo[5,4-d]azepine, 6-allyl-2-amino-4,5,7,8-tetrahydro-6H-thiazolo[5,4-d]azepine and the acid addition salts thereof is known from German Offenlegungsschrift No. 20 40 510. With regard to the preparation of these compounds, reference is made to the disclosure in the Offenlegungsschrift referred to hereinbefore.

The therapeutic system conveys the active substance transdermally into the bloodstream and brings about central α-stimulation which, if the active substance is 2-amino-6-ethyl-4,5,7,8-tetrahydro-6H-oxazolo[5,4-d]azepine, leads to the prevention or cure of high blood pressure, migraine, post-menopausal complaints, menstrual disorders or angina pectoris. It is also suitable for treating withdrawal symptoms, e.g. nicotine withdrawal symptoms. A preferred form of application is the treatment of high blood pressure by the transdermal administration of B-HT 933. If the active substance is 6-allyl-2-amino-4,5,7,8-tetrahydro-6H-thiazolo[5,4-d]azepine, the preferred indications are the lowering of the prolactin level, the treatment of Parkinson's disease and the treatment of schizophrenia.

Undesirable side effects such as may occur with oral treatment, e.g. considerable dryness of the mouth or sedation, are not observed or appear only in a very mild form. Skin incompatibilities or irritations such as may occur when chemical compounds are applied to the same patch of skin over a long period of time have not been observed either in animal experiments or in clinical trials on humans.

The absence of such side effects in the transdermal administration of 2-amino-6-ethyl-4,5,7,8-tetrahydro-6H-oxazolo[5,4-d]azepine is a major advantage in the treatment of growth disorders of children and young people. The present invention therefore also relates to the use of B-HT 933 for the preparation of a pharmaceutical composition for treating growth disorders. B-HT 933 or the acid addition salts thereof may be used to treat diseases based on a reduced secretion of growth hormone, as in subnormal growth, and in cases of reduced metabolism e.g. malnutrition, cachexia in tumours or during chemotherapy; chronic anoxia caused by respiratory insufficiency or cardiopathy, or kidney failure. Other types of indication are bone fractures, burns, wound healing and the speeding up of blood production. For diagnostic purposes, B-HT 933 may be used to stimulate the release of growth hormone and thereby establish whether sufficient growth hormone is present in the hypophysis.

Drugs for treating the above-mentioned indication (growth disorders) may be produced not only in the form of transdermal systems but also in the form of tablets, solutions, suspensions, suppositories, etc. With regard to the production of galenic preparations, reference is made to German Offenlegungsschriften Nos. 20 40 510 and 28 36 387. The therapeutically effective single dose for non-transdermal administration is between 2.5 and 50, preferably between 5 and 15 mg per dosage unit.

A preferred embodiment of the therapeutic system described may be produced by the following process:

The emulsion polymerised copolymer containing a proportion of basic end groups is dissolved together with the active substance in a suitable solvent, to form a dispersion which ranges from viscous to highly viscous. If the copolymer contains no basic end groups, a corresponding amount of an organic nitrogen-containing base may be added in order to stabilise the active substance. Suitable solvents include lower aliphatic alcohols, ethers, ketones, esters, hydrocarbons and halohydrocarbons, particularly those with a boiling point of below 100° C. which evaporate easily. Mixtures of solvents may also be used. The viscosities of the starting solutions may be varied by a suitable choice of solvent or solvent mixture. After a homogeneous solution (dispersion) is formed, this is poured onto the prepared backing layer consisting of a laminate of aluminium foil and a polyethylene film, so that the thickness of the layer of active substance is between 50 and 200 microns after drying. Drying usually takes place at ambient temperature or slightly elevated temperature and if desired it may be carried out under reduced pressure. If the compounds are light-sensitive, the therapeutic system may be prepared with the exclusion of light.

The film preparation may also be carried out continuously on a rolling train.

The film thus produced is then provided with a removable protective layer and packaged.

In another embodiment the dispersion may also be poured directly onto a suitably prepared backing layer.

The Examples which follow are intended to illustrate the invention without restricting it.

PREPARATION EXAMPLE 1

Composition:

| | |
|---|---|
| 9.744 g | Eudragit ® E 30 D (Messrs. Rohm of Darmstadt) |
| 0.600 g | Eudragit ® E 100 (Messrs. Rohm of Darmstadt) |
| 1.656 g | 2-amino-6-ethyl-4,5,7,8-tetrahydro-6H—oxazolo[5,4-d]azepine |
| 12.000 g | Solids |
| 6.000 g | Acetone |
| 22.000 g | Methanol |
| 100.000 g | of solution |

The Eudragit ® E 100 is dissolved in acetone, then the Eudragit 30 D and half the methanol are added and stirred in. When a homogeneous solution has formed, the active substance and the remaining methanol are added in batches. The resulting solution is poured onto a prepared backing layer using a film drawing apparatus (made by Messrs. Erichsen) and spread out with a doctor blade positioned at 0.6 mm. After 10 minutes' drying, another layer and then a third layer are applied with the same doctor blade position. After drying, a film is obtained having a thickness of 100 microns.

PREPARATION EXAMPLE 2

Composition:

| | |
|---|---|
| 9.144 g | Eudragit ® E 30 D |
| 1.200 g | Eudragit ® E 100 |
| 1.656 g | 2-amino-6-ethyl-4,5,7,8-tetrahydro-6Hoxazolo[5,4-d]azepine |
| 12.000 g | Solids |
| 66.000 g | Acetone |
| 22.000 g | Methanol |
| 100.000 g | Solution |

The film is prepared analogously to Example 1.

PREPARATION EXAMPLE 3

| Composition: | | |
|---|---|---|
| a | b | |
| 10.000 g | 10.620 g | Eudragit ® E 30 D |
| 0.300 g | 0.280 g | Eudragit ® E 100 |
| 0.800 g | 1.000 g | Active substance |
| 12.000 g | 12.000 g | Solids |
| 53.000 g | 53.000 g | Acetone |
| 10.000 g | 10.000 g | Methanol |

The films are prepared analogously to Example 1 but with a doctor blade position of 0.98 mm. The film was 200 microns thick.

PREPARATION EXAMPLE 4

| Composition: | | |
|---|---|---|
| A | B | |
| 7.533 g | 5.022 g | Eudragit ® E 30 D |
| 2.511 g | 5.022 g | Polyacrylate TG 29* |
| 0.300 g | 0.300 g | Triethanolamine |
| 1.656 g | 1.656 g | 2-amino-6-ethyl-4,5,7,8-tetrahydro-6H—oxazolo[5,4-d]azepine |
| 12.000 g | 12.000 g | Solids |
| 53.000 g | 53.000 g | Acetone |
| 10.000 g | 10.000 g | Methanol |

*This polyacrylate differs from Eudragit ® E 20 D solely by the monomer distribution, resulting in a higher glass temperature of +29° C.

The films were prepared analogously to the process described in Example 1, except that the dispersion was applied only twice, with a doctor blade position of 0.8 mm each time.

PREPARATION EXAMPLE 5

| Composition: | | | |
|---|---|---|---|
| A | B | C | |
| 10.224 g | 10.044 g | 9.744 g | Eudragit ® E 30 D |
| 0.120 g | 0.300 g | 0.600 g | Triethanolamine |
| 1.656 g | 1.656 g | 1.656 g | Active substance* |
| 12.000 g | 12.000 g | 12.000 g | Solids |
| 53.000 g | 53.000 g | 53.000 g | Acetone |
| 10.000 g | 10.000 g | 10.000 g | Methanol |

*In the above Example, both 2-amino-6-ethyl-4,5,7,8-tetrahydro-6H—oxazolo[5,4-d]azepine and also 6-allyl-2-amino-4,5,7,8-tetrahydro-6H—thiazolo[5,4-d]azepine were used as active substance.

The films were prepared analogously to Preparation Example 4.

PREPARATION EXAMPLE 6

Structure of product: circular plasters, 10 cm$^2$, 2 mg/cm$^2$, thickness 150 microns
  (a) Substrate: PE/Alu/film (1)
  (b) Active substance - polyacrylate layer (2)
  (c) Covering plaster with protective paper (3)
  (d) Film as in (a) used as the heat-sealed package.

Solution for Application

| | |
|---|---|
| 10.631 g | Eudragit ® E 30 D, air dried (88.59%) |
| 1.333 g | B-HT 933 BS (11.11%) |
| 0.036 g | Tris-(hydroxymethyl)-aminomethane(0.30%) |
| 12.000 g | Solids |
| 15.000 g | Methanol, (analytical grade) |
| 26.500 g | Acetone, (analytical grade) |
| 53.500 g | Solution (22.4%) |

(1) PE=polyethylene, Alu=aluminium
(2) Air dried Eudragit ® E 30 prepared from aqueous Eudragit E 30 dispersion
(3) Covering plaster, skin-coloured, 53×53 mm with white covering paper.

Equipment

Magnetic stirrer, Erichsen film-drawing apparatus with doctor blade and dark hood, punch with an area of 10$^2$, film welding apparatus.

Production

Preparation

The Erichsen apparatus is fitted with wrapping film and sucked flat by the application of vacuum.

Solution of active substance

The acetone and half the methanol are put in, the tris(hydroxymethyl)aminomethane is dissolved therein and the Eudragit ® E 30 D is added with vigorous stirring and stirred until completely dissolved.

The B-HT 933 BS is dissolved in half the remaining methanol, stirred and rinsed with the other half.

Films

The solution is applied in one go with a doctor blade position of 1.4 mm. After drying, a film containing the active substance is obtained which contains about 18.0 mg/cm$^2$, corresponding to a thickness of about 150 microns.

Punching and packaging

The sheets of film are immediately stamped out, packed in the covering plasters and sealed in prepared bags consisting of AL/PE film under a current of nitrogen.

The in vitro release of active substance was determined in a modified USP-XVII tester; pieces of film measuring about 3 cm$^2$ and covered on their backs were placed in 10 ml of warm (32° C.) demineralised water then gently mixed and analysed at certain intervals of time.

The following Table shows the quantity of active substance released after 8, 24 and 48 hours, in mg an %.

Release of the film prepared according to Preparation Example 1:

| Experiment No. | 8 hours | 24 hours | 48 hours |
|---|---|---|---|
| 1 | 3.1743 | 3.9488 | 4.1642 mg |
|   | 73.85 | 91.87 | 96.88% |
| 2 | 3.2186 | 4.0603 | 4.3036 mg |
|   | 72.61 | 91.59 | 97.08% |
| 3 | 2.4225 | 3.6707 | 4.0083 mg |
|   | 57.97 | 87.83 | 95.91% |
| Average | 2.9385 | 3.8933 | 4.1587 mg |
|   | 68.14 | 90.43 | 96.63% |

Release of the film prepared according to Preparation Example 2.

| Experiment No. | 8 hours | 24 hours | 48 hours |
|---|---|---|---|
| 1 | 2.5128 | 4.1762 | 4.5720 mg |
|   | 52.75 | 87.67 | 95.97% |
| 2 | 2.4041 | 4.0224 | 4.4049 mg |
|   | 52.38 | 87.65 | 95.98% |
| 3 | 2.4312 | 3.9532 | 4.3255 mg |
|   | 54.02 | 87.83 | 96.11% |
| Average | 2.4494 | 4.0506 | 4.4341 mg |
|   | 53.05 | 87.72 | 96.02% |

Release of the film prepared according to Preparation Example 3a.

| Experiment No. | 8 hours | 24 hours | 48 hours |
|---|---|---|---|
| 1 | 0.4028 | 0.9133 | 1.3914 mg |
|   | 15.05 | 34.13 | 51.99% |
| 2 | 0.4153 | 1.2854 | 1.9628 mg |
|   | 13.02 | 40.29 | 61.52% |
| 3 | 0.4272 | 0.9261 | 2.1449 mg |
|   | 11.64 | 25.23 | 58.44% |
| Average | 0.4165 | 1.0281 | 1.9253 mg |
|   | 12.90 | 31.90 | 58.56% |

Release of the film prepared according to preparation Example 3b.

| Experiment No. | 8 hours | 24 hours | 48 hours |
|---|---|---|---|
| 1 | 0.7576 | 1.9396 | 2.5619 mg |
|   | 21.00 | 53.76 | 71.01% |
| 2 | 0.7467 | 2.0123 | 2.7526 mg |
|   | 19.11 | 51.50 | 70.45% |
| 3 | 0.7380 | 2.4632 | 3.8498 mg |
|   | 16.42 | 54.79 | 85.63% |
| 4 | 0.7356 | 1.8289 | 2.4715 mg |
|   | 19.02 | 47.28 | 63.89% |
| Average | 0.7445 | 2.0610 | 2.9090 mg |

| Experiment No. | 8 hours | 24 hours | 48 hours |
|---|---|---|---|
| | 18.89 | 51.83 | 72.75% |

Clinical trials with 2-amino-6-ethyl-4,5,7,8-tetrahydro-6H-oxazolo[5,4-d]azepine as active substance.

After application of a plaster containing 2.3 mg of active substance per 2.5 cm² to three healthy male subjects, the plasma concentrations of 2-amino-6-ethyl-4,5,7,8-tetrahydro-6H-oxazolo[5,4-d]azepine were measured at intervals of 24 hours.

Five plasma samples were taken from each test subject at times 0, 24, 48, 72 and 96 hours after the start of application.

RIA (radio immuno assays) were used as the analytical method, each sample being measured twice. Table 1 shows all the individual values measured.

TABLE 1

Concentrations (ng/ml) of the active substance in the plasma of 3 test subjects after application of a plaster containing 2.3 mg of active substance per 2.5 cm².
Results of the double measurements by RIA

| Time | Subject No. 1 | 2 | 3 |
|---|---|---|---|
| 0 h | 0.00 | 0.00 | 0.00 |
| | 0.00 | 0.00 | 0.00 |
| 24 h | 0.28 | 0.10 | 0.14 |
| | 0.31 | 0.08 | 0.13 |
| 48 h | 0.41 | 0.31 | 0.29 |
| | 0.41 | 0.30 | 0.31 |
| 72 h | 0.30 | 0.40 | 0.17 |
| | 0.28 | 0.35 | 0.16 |
| 96 h | 0.26 | 0.22 | 0.18 |
| | 0.26 | 0.22 | 0.18 |

No side effects or skin irritations were observed in any of the subjects.

We claim:

1. A transdermal patch comprising a reservoir layer, a backing layer for containing said reservoir layer and means for securing said patch to the skin of a subject, wherein said reservoir layer comprises an active substance selected from the group consisting of 2-amino-6-ethyl-4,5,7,8-tetrahydro-6H-oxazolo[5,4-d]azepine and 6-allyl-2-amino-4,5,7,8-tetrahydro-6H-thiazolo[5,4-d]azepine in a pharmaceutically acceptable matrix comprising an emulsion polymerized polymer or copolymer and a stabilizer selected from the group consisting of (a) copolymers formed from a neutral methacrylic acid alkyl ester, wherein the alkyl is selected from the group consisting of methyl and butyl and dimethylaminoethylmethacrylate and (b) organic nitrogen containing bases of the formula

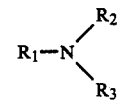

wherein $R_1$, $R_2$ and $R_3$ are each hydrogen or branched or unbranched alkyl or hydroxyalkyl of 1 to 5 carbon atoms.

2. The transdermal patch of claim 1 wherein said emulsion polymerized polymer or copolymer is selected from the group consisting of polyvinyl chloride, polylactides, polystyrene, polyvinyl acetate, polybutadiene, polyacrylonitrile, polyvinylesters, polyvinylethers and copolymers thereof.

3. The transdermal patch of claim 1 wherein said emulsion polymerized polymer is a copolymer of a methyl or ethyl ester of acrylic and methacrylic acid.

4. The transdermal patch of claim 1 wherein said stabilizer is an emulsion polymerized copolymer with basic end groups which is present in an amount of from about 1 to 50% by weight, based upon the total quantity of polymer in said reservoir.

5. The transdermal patch of claim 4 wherein said stabilizer comprises a copolymer of dimethylaminoethylmethacrylate and a neutral methacrylic acid ester, with an average molecular weight of about 150,000.

6. The transdermal patch of claim 1 wherein said stabilizer is an organic nitrogen containing base which is present in the amount of about 0.5 to 5% by weight, based upon the quantity of active substance in said reservoir.

7. The transdermal patch of claim 6 wherein the organic base is selected from the group consisting of isopropylamine, triethylamine and tris (hydroxymethyl)-aminomethane.

8. The transdermal patch of claim 1 wherein the amount of said active substance is in the range of from about 0.5 to about 6 mg per cm² and wherein the thickness of said reservoir layer is between about 40 and 300 microns.

* * * * *